US006650489B2

(12) United States Patent
Ravich et al.

(10) Patent No.: US 6,650,489 B2
(45) Date of Patent: *Nov. 18, 2003

(54) GEM IDENTIFICATION VIEWER

(75) Inventors: Gilbert N. Ravich, Lawndale, CA (US); Shane Elen, Oceanside, CA (US); James Shigley, Temecula, CA (US)

(73) Assignee: Gemological Institute of America, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/197,069

(22) Filed: Jul. 17, 2002

(65) Prior Publication Data

US 2002/0180952 A1 Dec. 5, 2002

Related U.S. Application Data

(63) Continuation of application No. 09/931,907, filed on Aug. 16, 2001, now abandoned, which is a continuation of application No. 09/362,762, filed on Jul. 28, 1999, now Pat. No. 6,292,315.
(60) Provisional application No. 60/094,345, filed on Jul. 28, 1998.

(51) Int. Cl.[7] .................................................. G02B 5/22
(52) U.S. Cl. ............................ 359/885; 63/32; 501/86; 356/30; 356/301
(58) Field of Search ............................ 359/885; 29/10; 63/26, 32; 501/86; 356/30, 301

(56) References Cited

U.S. PATENT DOCUMENTS

| 4,577,927 | A | * | 3/1986 | Raney | .................. | 359/803 |
| 4,799,786 | A | | 1/1989 | Gerrard | | |
| 5,118,181 | A | * | 6/1992 | Yifrach | ..................... | 356/30 |
| 5,835,200 | A | * | 11/1998 | Smith | ...................... | 356/30 |
| 5,835,205 | A | * | 11/1998 | Hunter | ..................... | 356/30 |
| 6,014,208 | A | * | 1/2000 | Welbourn | ............... | 356/237.1 |
| 6,292,315 | B1 | * | 9/2001 | Ravich | ................... | 359/885 |

* cited by examiner

*Primary Examiner*—John Juba
*Assistant Examiner*—Leo Boutsikaris
(74) *Attorney, Agent, or Firm*—Gray Cary Ware & Freidenrich

(57) ABSTRACT

A gem identifying device using filtered transmitted light for use in distinguishing type-I colorless diamonds from type II colorless diamonds, and natural diamonds and gems from synthetic or treated diamonds and gems.

20 Claims, 1 Drawing Sheet

GEM IDENTIFICATION VIEWER

Figure 1:
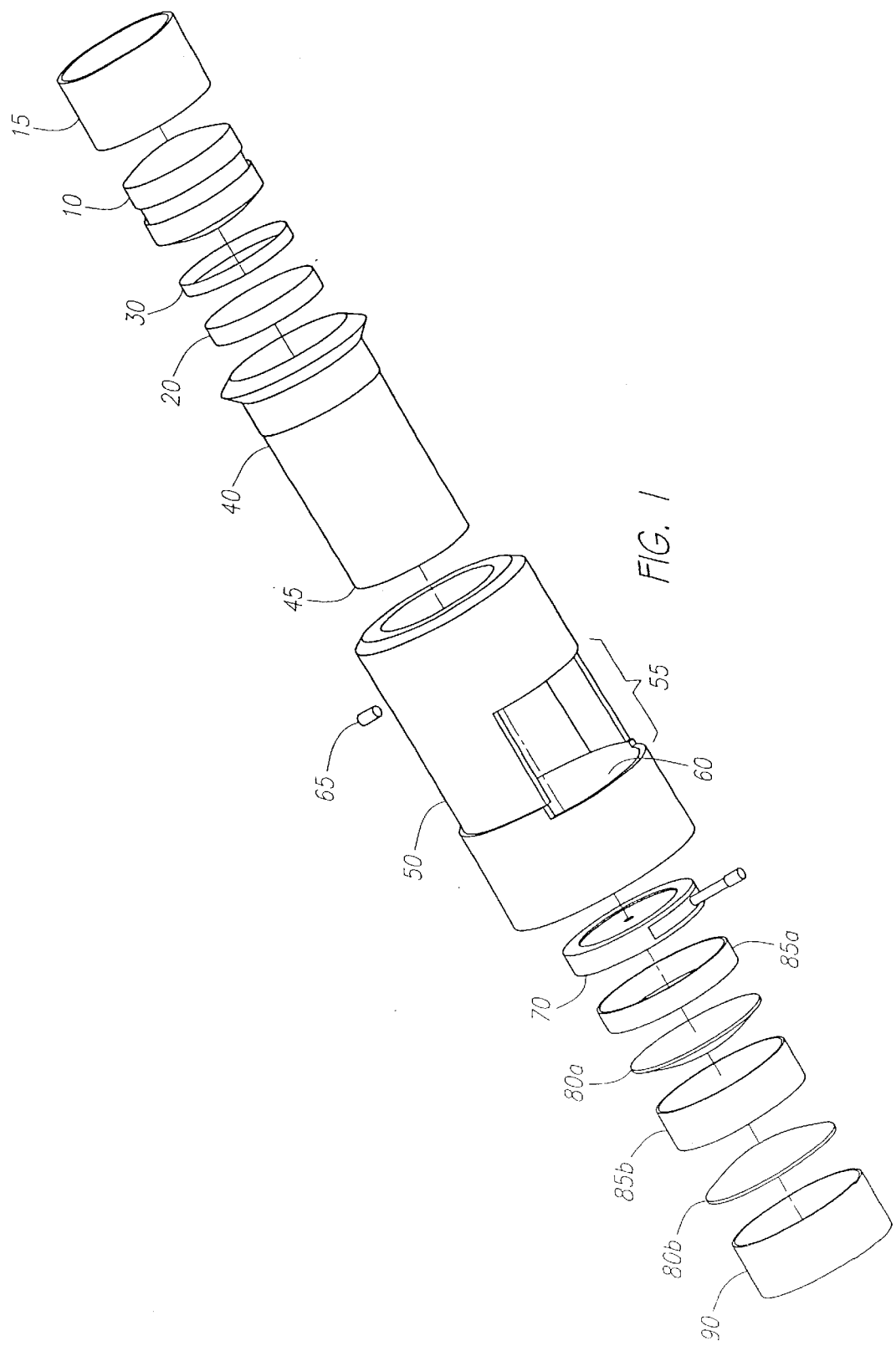

This application is a Continuation of U.S. patent application Ser. No. 09/931,907, filed Aug. 16, 2001 now abandoned, which is a Continuation of U.S. patent application Ser. No. 09/362,762, filed on Jul. 28, 1999, now U.S. Pat. No. 6,292,315, which claims benefit of U.S. Provisional Application Ser. No. 60/094,345, filed Jul. 28, 1998, all of which are incorporated herein by reference.

BACKGROUND OF THE INVENTION

The identification of natural, synthetic, and laboratory-treated gemstones presents an ongoing challenge to gemologists and jewelers. To address this problem, practical instruments are needed that will enable gemstones to be distinguished from one another quickly and easily.

Gemologists have traditionally used the visible spectra of gemstones to help in their identification. When light passes through a gemstone, a portion of the visible spectrum of a gemstone may be observed by means of the spectroscope enabling a viewer, to see the pattern of sharp absorption lines and broad regions of absorption and transmission that are often characteristic of a particular gem material.

SUMMARY OF THE INVENTION

This invention uses a selective filter to distinguish two different gemstones that may be similar in color, but differ in their visible spectra. One embodiment of the invention comprises:

a) a light source;

b) a glass plate on which the gemstone is placed for observation;

c) an iris diaphragm to restrict light from being transmitted around the edge of the gemstone being examined;

d) a selective filter, chosen depending upon the spectra of the two gemstones to be distinguished;

e) and a lens to view the gemstone in transmitted light.

By means of this invention, and the proper selection of the filter, it is possible to directly observe whether or not a gemstone is transmitting the light passed by the filter. By proper selection of the filter, one gemstone will appear to transmit the light, and it will appear bright, while the other gemstone will not transmit the light, and it will appear dark. The idea of gem identification by using filtered transmitted light is one novel aspect of the invention. The apparatus also provides for a convenient and expedient gem identification process.

There are several possible applications of this invention. Specific applications include distinguishing:

a) type-I a colorless diamonds which occur in nature from type-ii-a colorless diamonds (which are rare in nature and can be produced in the laboratory). For this application, the invention will make use of a bandpass filter with a center frequency of about 415 nanometers. The type I-a colorless diamonds will transmit this light and thus appear bright in the viewfinder. In contrast, a type II a colorless diamond will appear dark. Such a test will allow jewelers to quickly determine whether further evaluation for synthetic diamond material is required;

b) diamonds that have been treated with a high refractive index glass to hide the visibility of surface-reaching fractures from non-treated diamonds. Diamonds that have been treated with a high refractive index glass have an altered absorption pattern compared to untreated diamonds. The transmission based gem detection system described herein deploys a band-pass filter which selects for high refractive index glass;

c) colorless diamond from colorless synthetic mossanite (silicon carbide—a new diamond imitation material). For this application, this instrument deploys a filter which filters out light at wavelengths above about 430 nanometers. Diamond is relatively transparent in this region below 430 nanometers, while moissanite is more opaque and light absorbing for this region. Thus, when the selective filter permits illumination of the gem only with light below 430 nanometers, the diamond appears bright through the viewer. The moissanite appears dark under the same circumstances.

d) natural color gemstones from laboratory-treated colored gemstones and from synthetic colored gemstones.

No other similar gem-testing instruments are known. There are several colored lenses that are sold by Hanneman Gemological Institute of Castro Valley, Calif., that distinguish certain types of colored gemstones based upon how the gemstones appear in reflected white light when viewed through the lens. For example, such lenses may be used to separate topaz from aquamarine gems. There is also a device, known as a phosphorescope used for visual observation, and an instrument used for measurement of differences in transparency of gemstones to short-wave ultraviolet radiation. However, none of these products work on the basis of the same principle as the instrument described herein.

DETAILED DESCRIPTION OF THE DRAWINGS

FIG. 1 is a schematic, exploded view of one embodiment of the gem identification viewer.

DETAILED DESCRIPTION OF THE INVENTION

In a preferred embodiment, shown in FIG. 1, the gem identification viewer comprises a viewing lens 10 which is aligned with filter 20 to form a filter assembly. The viewing lens 10, which is preferably a magnification lens, is separated from the filter 20 by a spacer 30. The filter assembly is deposited in eyepiece 40 and a top ring 15 is placed over lens 10 to further secure the filter assembly within the eyepiece 40. The eyepiece 40 has a distal end 45 which is aligned within housing 50 through the top of said housing. Housing 50 may comprise a hollow tube with a generally spherical cross-section. Housing 50 contains side opening 55 to permit placement of the gem on the transparent observation plate 60. The eyepiece 40 is secured within housing 50 by virtue of a ball plunger 65. The bottom of housing 50 is aligned with iris diaphragm 70 which contains an iris opening such that light transmitted into the housing 50 from its distal end is restricted in a way that does not allow light to be transmitted around the edge of the gemstone to be examined. Optionally, the iris opening is adjustable. The iris diaphragm is aligned with first and second condenser lenses 80a and 80b which are oriented so as to condense light entering into the housing from the bottom opening. The diaphragm 70 and the first condenser lens 80a are separated by spacer 85a so as to protect the edge of the lens. The first and second lenses are similarly separated by spacer 85b. The second condenser lens 80b is secured by bottom ring 90. Bottom ring 90 is preferably a tubular ring shape which has the inner diameter of a handheld flashlight.

According to a preferred method of gem identification, the user places a flashlight or other light source underneath the bottom ring 90 of the gem identification viewer so that light is transmitted up through the condenser lenses 80a and 80b, through the iris diaphragm 70 and through the viewing platform 60. A gem is placed on the viewing platform 60 and, while viewing through the viewing lens 10, the iris diaphragm 70 is adjusted so that little or no light is transmitted to the viewing lens 10 from outside the edge of the gem. This represents a significant advantage over reflected light observation. The viewer then notes the brightness of the gem. By proper selection of the filter, one gemstone will appear to transmit the light and it will appear bright, while the other gemstone will not transmit the light and it will appear dark. The amount of light that is passed through both the gem and the filter 20 thereby permits ready visual identification of gem type and gem authenticity as given above. For example, colorless synthetic moissanite, a new diamond imitation material, may be distinguished from natural diamond by a jeweler using the described method with a low pass filter having about a 430 nanometer cutoff.

In alternate embodiments, the location of the filter may be distal to the housing 50 relative to viewing lens 10. That is to say, the light may be filtered prior to transmission through the gem. Alternatively, the invention may deploy a monochromatic source at the critical wavelength either with or without a filter. The source should be portable, however, and thus sources requiring large power supplies are disfavored. Other embodiments may employ a light polarizing prism in place of the filter. By polarizing the source light before it reaches the gem, the transmitted light will be similarly polarized. Thus, a polarizing optical element placed in front of the lens can preferentially select out radiation transmitted with the same polarization. This may be used to distinguish gems based on their effect of polar qualities of light, or simply to act as a polar filter for filtering out non-critical wave length light while letting pre-polarized source light to be identified by a pre-lens polar optical element. The same principles may be employed using phase modulated light to distinguish gems. Although modifications and changes may be suggested by those skilled in the art, it is the intention of the inventors to embody all warranted changes which reasonably come within the scope of their contribution to the art.

What is claimed:

1. A gemstone identifying apparatus comprising:
   a housing having an opening for receiving light;
   a surface within the housing for placement of a gemstone being examined;
   a filter selected according to the light transmission spectra of the gemstone; and
   a viewing lens for viewing light passing through the gemstone and the filter.
2. The apparatus of claim 1, wherein said filter is a band pass filter with a center of about 415 nm.
3. The apparatus of claim 1, further comprising an iris diaphragm for restricting light from being transmitted around the edge of the gemstone.
4. The apparatus of claim 1, wherein said filter is selected according to the light transmission spectra of a gemstone to be distinguished from the gemstone being examined.
5. The gem identifying apparatus of claim 3 wherein the iris diaphragm is adjustable.
6. An apparatus for examining a gemstone, comprising:
   a housing;
   a transparent plate contained within the housing for placement of a gemstone being examined;
   a light-restricting iris diaphragm aligned at a distal end of the housing and including an opening for receiving light;
   an eyepiece within the housing and having a viewing lens; and
   a filter having filtering characteristics based on light transmission spectra of a gemstone being distinguished with the gemstone being examined.
7. The apparatus of claim 6, wherein the filtering characteristics of the filter are selectable.
8. The apparatus of claim 6, wherein the iris diaphragm is adjustable.
9. The apparatus of claim 6, wherein the iris opening is adjustable.
10. An apparatus for examining a gemstone, comprising:
    a housing having a transparent plate for placement of a gemstone being examined;
    an iris diaphragm coupled to a bottom of the housing for restricting light from being transmitted around the edge of the gemstone, and including an iris opening for transmitting light;
    an eyepiece coupled through a top of the housing and including:
       a filter for filtering light which passes through the transparent plate and the gemstone; and
       a lens for viewing light which passes through the filter.
11. A method for examining a gemstone, comprising:
    placing a gemstone on an observation plate within a housing;
    receiving light through an iris opening in an iris diaphragm coupled to a bottom of the housing;
    passing light from the iris opening through the gemstone being examined, wherein the iris diaphragm restricts light from being transmitted around the edge of the gemstone;
    filtering light passing through the gemstone based on a light transmission spectra of a gemstone to be distinguished; and
    viewing light which passes through the gemstone.
12. A method for examining a gemstone, comprising:
    transmitting a selectable amount of light to the gemstone through an adjustable iris opening defined in an iris diaphragm, wherein the iris diaphragm restricts light from being transmitted around the edge of the gemstone;
    filtering light from the iris opening which passes through the gemstone, wherein the filter is based on a light transmission spectra of a gemstone to be distinguished; and
    viewing light which passes through the gemstone.
13. A gemstone identifying apparatus, comprising:
    a surface for placement of a gemstone;
    an iris diaphragm for restricting light from being transmitted around the edge of the gemstone being examined;
    a filter to filter light passing through the gemstone; and
    a lens for receiving light filtered by the filter and passing through the gemstone;
    wherein the filter is a polarizing prism.
14. The gemstone identifying apparatus of claim 13, wherein the filter is a selective filter, chosen depending upon light transmission spectra of one of at least two gemstones to be distinguished.
15. A gemstone identifying apparatus, comprising:
    a surface for placement of a gemstone;
    an iris diaphragm for restricting light from being transmitted around the edge of the gemstone being examined;

a low pass filter to filter light passing through the gemstone; and a lens for receiving light filtered by the filter and passing through the gemstone;

wherein the low pass filter has a cut-off of about 430 nm.

16. An apparatus for use with a light source for observing a gemstone, comprising:

a housing having an iris opening for receiving light from the light source;

a surface within the housing on which the gemstone is placed so as to receive light from the iris opening;

a filter to filter light received by the gemstone; and a lens positioned to receive light passing through the gemstone;

wherein the filter is a polarizing prism.

17. The apparatus of claim 16, wherein the filter is selected depending upon the spectra of one of at least two gemstones to be distinguished.

18. The apparatus of claim 16, wherein the surface is a glass plate.

19. The apparatus of claim 16, wherein the lens is positioned distal from the iris opening.

20. An apparatus for use with a light source for observing a gemstone, comprising:

a housing having an iris opening for receiving light from the light source;

a surface within the housing on which the gemstone is placed so as to receive light from the iris opening;

a low pass filter to filter light received by the gemstone; and a lens positioned to receive light passing through the gemstone;

wherein the low pass filter has a cut-off of about 430 nm.

* * * * *